United States Patent [19]

Valenti et al.

[11] Patent Number: 5,830,489
[45] Date of Patent: Nov. 3, 1998

[54] PROTEIN PREPARATION FOR THE PREVENTION AND THERAPY OF PERIODONTITIS

[75] Inventors: Piera Valenti, Rome; Giovanni Antonini, Caprarola, both of Italy

[73] Assignee: Pfizer Inc., New York, N.Y.

[21] Appl. No.: 448,535

[22] PCT Filed: Dec. 15, 1993

[86] PCT No.: PCT/EP93/03571

§ 371 Date: Oct. 11, 1995

§ 102(e) Date: Oct. 11, 1995

[87] PCT Pub. No.: WO94/13318

PCT Pub. Date: Jun. 23, 1994

[30] Foreign Application Priority Data

Dec. 16, 1992 [IT] Italy ................. RM92A0900

[51] Int. Cl.$^6$ .............. A61K 7/16; A01N 25/00
[52] U.S. Cl. .................... 424/405; 424/49; 424/422; 424/440
[58] Field of Search ................ 424/405, 422, 424/49, 440; 514/900, 901, 902

[56] References Cited

U.S. PATENT DOCUMENTS 5,202,113 4/1993 London .................. 424/54
5,422,108 6/1995 Mirkov et al. ............ 424/94.61

Primary Examiner—Thurman K. Page
Assistant Examiner—Kathryne Shelborne
Attorney, Agent, or Firm—Peter C. Richardson; Paul H. Ginsburg; Grover F. Fuller, Jr.

[57] ABSTRACT

The present invention relates to a topical protein preparation to be used for the therapy of periodontitis and diseases of the teeth and of the tissues of the oral cavity, comprising a mixture of transferrin with at least one protein selected from albumins, lysozymes, protease inhibitors, and mixtures thereof.

13 Claims, No Drawings

PROTEIN PREPARATION FOR THE PREVENTION AND THERAPY OF PERIODONTITIS

TECHNICAL FIELD

The present invention relates to a protein preparation for preventing and curing bacterial pathologies and disorders of the oral cavity, in particular periodontitis and dental caries.

BACKGROUND ART

Periodontal disease comprises a group of disorders that affect the supporting structures of the teeth, leading to their progressive pathologic-anatomical deterioration and ultimately to a possible complete loss of the dental elements. From an epidemiological point of view, it has been stressed that periodontal disease, in its various forms, affects a considerable number of individuals (30–40% between 25 and 40 years of age, and 60–70% of individuals over 40).

From a clinical point of view, the disease is characterized by gum inflammation, edema, provoked or spontaneous bleeding, apical migration of the connective attachment, with the forming of periodontal pockets, bone reabsorption, marked dental mobility and, in some cases, gum recession.

A few years ago it was demonstrated that periodontitis, in all of its clinical forms, has a bacterial etiology and that the microorganisms that most frequently cause this disease are Gram-negative obligate anaerobes such as *Porphyromonas gingivalis*.

Dental caries is instead a demineralizing disorder that affects teeth at all levels and can cause extensive crown mutilations, bacterial disorders of the periapical tissues or even loss of the affected dental elements. Approximately 50% of adult individuals have at least four caries-related lesions treated and to be treated, and approximately 30% of adult individuals have over 50% of their teeth affected by caries.

Clinically, the disease is characterized by demineralization of the dental enamel and of the dentin in various stages of progress, until it affects the pulp space. When the lesion passes beyond the enamel-dentin border, a phlogistic reaction of the pulp tissues is constantly observed, with the formation of reaction dentin in some cases.

It has been demonstrated that caries is produced by an acid attack on the dental surfaces, linked to the fermentative metabolism of sugars in the diet on the part of some bacterial species capable of adhering to the dental enamel. The species most frequently responsible for caries is *Streptococcus mutans*.

It has been extensively demonstrated that the ability of microorganisms to produce infections is linked to the possibility of their adhering specifically or non-specifically to the different tissues, which allows the microorganisms to subsequently colonize the tissues extensively. In the pathogenesis of the most common infections of the oral cavity, bacterial adhesion and subsequent colonization of dental surfaces and soft tissues is undoubtedly of primary importance. The dental surface is normally covered by a thin film (acquired film) formed by the salivary glycoproteins that adsorb selectively on the surface of the tooth, allowing colonization on the part of specific microorganisms and preventing it to others. Furthermore, saliva is constituted by a series of protein-based substances having an antibacterial activity. Consequently, by possessing an antibacterial activity and an anti-adhesive activity of a competitive type against pathogenic species, saliva has a very important role in the qualitative and quantitative control of the microbial flora of the oral cavity. From the above it is evident that the optimum compound to be administered to prevent and cure microbial affections of the oral cavity must have an antibacterial and anti-adhesive activity like the protein components of saliva.

Currently, periodontitis and caries are treated by mechanically removing the dental plaque and the damaged tissues and by surgically correcting and reconstructing the damaged structures. Furthermore, restoration of optimum oral hygiene conditions by using mouthwashes is very important in preventing and curing these affections. However, treatment with mouthwashes based on disinfectant substances is not the ideal adjuvant treatment in preventing and curing these disorders. These substances (e.g. chlorhexidine) in fact have a systemic toxicity and a marked incidence of side effects that limit their use; furthermore, these substances do not prevent adhesion of microorganisms to dental surfaces.

DISCLOSURE OF THE INVENTION

The present invention relates to a protein formula or preparation for the prevention and therapy of periodontitis and diseases of the teeth and of the tissues of the oral cavity, characterized in that it comprises a mixture of proteins comprising at least one transferrin in a mixture with at least one additional protein selected from the group comprising albumins, lysozymes, protease inhibitors, and mixtures thereof; with the proviso that when said mixture does not contain either an albumin or a protease inhibitor, the transferrin and lysozyme components of the mixture are the only antibacterial, anti-adhesive or anti-invasive agents in said preparation.

It has been observed that the preparation according to the invention performs a synergistic activity and an antibacterial, anti-adhesive, anti-invasive and anti-protease activity that is not only higher than that of the individual proteins forming the mixture but also higher than that of salivary proteins.

Since at the present time there is no animal species that is considered universally valid for the testing of substances for preventing and curing periodontitis, the following examples were applied to "in vitro" models that are generally accepted for the testing of adjuvants in preventing and curing periodontitis and other bacterial disorders of the oral cavity.

Anti-adhesive activity is demonstrated by the reduced binding of the microorganisms to a substance (hydroxyapatite) that simulates the dental surface; antibacterial activity is demonstrated by a bacteriostatic and/or bactericidal effect on specific bacterial genera; anti-protease activity is verified by a higher anti-adhesive and antibacterial activity of the complete protein formula with respect to the formula without inhibitors, which is subject to the aggression on the part of microbial proteases. The anti-adhesive and antibacterial effectiveness of the protein formula according to the present invention is in fact higher than that obtained with its individual components, thus showing a synergistic activity due to the simultaneous presence of the different proteins that characterize the formula described herein.

It has been observed that the quantitative ratios of the protein compounds in the preparations according to the invention can vary within wide limits, since these compounds already start having a synergistic effectiveness at low concentrations in the mixture.

In particular, in binary mixtures of transferrin with an albumin or a lysozyme, each one of the protein compounds can be present at a concentration of 5 to 95% by weight with respect to the protein mixture. For example, preparations according to the invention can contain 10–40% transferrin and 90–60% albumin, or 90–60% transferrin and 10–40% lysozyme; the amounts may also be determined by economic factors, for example by the cost of the proteins used.

In binary mixtures of transferrin with one or more protease inhibitors, said inhibitors can have concentrations of 1 to 20%, for example 2 to 10%, by weight.

In preferred ternary mixtures of transferrin with albumin and lysozyme, total concentrations of transferrins and albumins can vary from 5 to 90% by weight, whereas lysozymes can be present at concentrations of 2 to 90% by weight. For example, a ternary mixture can comprise 10–40% transferrin, 40–85% albumin and 2–20% lysozyme. When using a ternary mixture of transferrin with protease inhibitors and with an additional protein selected from albumins and lysozymes, the protease inhibitors are present at a concentration of 1 to 20% by weight, for example 2 to 10%, whereas the concentrations of each one of the other protein compounds can vary between 5 and 94%, for example from 20 to 75%, with respect to the mixture.

WAYS OF CARRYING OUT THE INVENTION

A particularly preferred preparation according to the invention is a mixture of all four types of protein compounds mentioned above, and thus a mixture of at least one transferrin at a concentration of 5 to 92%, of at least one lysozyme at a concentration of 2 to 80%, of at least one albumin at a concentration of 5 to 92%, and of at least one protease inhibitor at a concentration of 1 to 20%, these concentrations being given by weight with respect to the protein mixture. For example, such a quaternary mixture can comprise one or more transferrins at an overall concentration of 10–50%, for example of 15–25%, one or more albumins at an overall concentration of 40–84%, for example of 60–75%, one or more lysozymes at an overall concentration of 5–30%, for example of 5–10%, and one or more protease inhibitors at a total concentration of 1–10%, for example of 2–5%, by weight.

By way of example, a preparation according to the invention can comprises 75% albumin, 17% transferrin, 5% lysozyme and 3% protease inhibitors.

When the preparation according to the invention comprises more than one compound of the class of transferrins, lysozymes, albumins or protease inhibitors, their combined amount totals the concentrations given above for each class of protein compounds.

The examples reported above show that the formula according to the present invention can be considered optimum, with respect to treatments currently in use, for the prevention and cure of periodontitis and other bacterial disorders of the oral cavity. Furthermore, the extremely low toxicity of the proteins contained in the formula according to the present invention is well-known, since these are extracted "natural" substances (but also chemically synthesizable) which are very similar, in their amino acid composition and structural configuration, to the homologous proteins that are normally present in the human and animal body. This is an additional advantage of the formula according to the present invention with respect to the chemicals currently used in periodontitis treatment.

The proteins that can be used in the formula according to the present invention can therefore be extracts or can be obtained by recombinant-DNA technology or also by chemical synthesis.

The term albumin designates, in the present invention, a glycoprotein or deglycosylated protein having characteristics similar to those of human albumin; the formula according to the present invention can be produced with any one of the proteins of various origin that are commonly termed "albumins" and are commercially available: serum albumin and lactalbumin from humans, bovines, cats, dogs, rabbits, horses, sheep, goats, serum albumin and ovalbumin from turkeys, chickens, pigeons, etc.

The term transferrin designates a glycoprotein or a corresponding deglycosylated protein capable of chelating two $Fe(III)$ atoms per molecule, having structural and functional characteristics similar to those of human lactoferrin, characterized by a known antibacterial activity; the formula according to the present invention can be produced with any one of the proteins of various origin commonly termed "transferrins" that are commercially available: serum transferrin and lactoferrin from humans, bovines, cats, dogs, rabbits, horses, sheep, goats, serum transferrin and ovotransferrin from turkeys, chickens, pigeons etc.

The term lysozyme designates a protein having structural and functional characteristics similar to those of human lysozyme, which is characterized by a known enzymatic bactericidal activity against Gram-positive bacteria; the formula according to the present invention can be produced with any one of the proteins of various origin commonly termed "lysozyme" that are commercially available: lysozyme from humans, bovines, horses, turkeys, chickens, etc.

The term protease inhibitors designates a class of proteins having characteristics similar to those of human trypsin and chymotrypsin inhibitors, characterized by the ability to inhibit the protease activity of trypsin and chymotrypsin; the formula according to the present invention can be obtained with any one of the proteins of various origin commonly termed "trypsin and chymotrypsin inhibitors" that are commercially available: trypsin and chymotrypsin inhibitors from bovines, soybean seeds, chickens, turkeys, etc.

There are many proteins pertaining to the classes of albumins, transferring, lyzozymes and protease inhibitors, which are available on the market and which can be used in the preparation of this invention. Illustrative of such commercial proteins are for example those sold by SIGMA Chemical Co., St. Louis, U.S.A.

The protein formula according to the present invention can be obtained and stored in liquid form, as solutions at a concentration of 0.1 to 10%, e.g. 1 to 5%, weight/volume (g/ml) of the protein mixture in solvents acceptable for pharmaceutical use, in particular water or hydro-alcoholic solvents such as water-ethanol mixtures, or in solid form (lyophilized, dried, frozen) and in the other commonly known forms of storage: for example immobilized or adsorbed on an inert support commonly used in the pharmaceutical field.

The protein preparation according to the invention can thus be used in the liquid form, as a rinse or mouthwash, or in solid form, such as in powder or granular form to be dissolved in water for preparing a mouthwash just before use, with the concentrations specified above. Alternatively) it is possible to incorporate the protein mixture of the invention in a toothpaste or in a formulation to be chewed, such as chewing gum, tablets, pastilles, lozenges, etc. in a concentration of 1 to 60% by weight of the total formulation.

In its form ready-for-use the preparation according to the invention can also comprise further conventional antibacterial and antiplaque compounds as well as carriers, fillers, flavouring agents, preservatives, surfactants, colorants and other adjuvants selected from those conventionally used for the various liquid or solid form preparations for oral topical use.

Thus, formulations for oral use according to the invention can also comprise further anti-bacterial and antiplaque compounds, such as quaternary ammonium compounds with one long chain alkyl on the nitrogen atom, alkali metal pyrophosphates and orthophosphates halogenated bisphenols and halogenated diphenyl ethers, sodium benzoate, sodium salicylate, etc.

Liquid rinse formulations according to the invention can further comprise humectants, e.g. glycerin, sorbitol, xylitol, propylene glycol, etc., flavours, e.g. oil of spearmint, peppermint or cinnamon, menthol, methyl salicylate, etc., sweetening agents, e.g. aspartame, saccharin, dextrose, cyclamate, wintergreen, etc., thickening agents, e.g. xanthan gum, carrageenin, carboxy methyl cellulose, etc., detergent builders, e.g. sodium carbonate, bicarbonate, sulfate or borate, etc., surfactants either of anionic type, such as salts of higher fatty acid monoglyceride monosulfates, higher alkyl sulfates, alkyl aryl sulfonates, higher alkyl sulfoacetates, etc., or of non-ionic type, such as block polymers of polyoxyethylene and polyoxypropylene, polyethylene oxide condensates of alkyl phenols, products of condensation of ethylene oxide with propylene oxide and ethylene diamine, long chain tertiary amine oxides, long chain dialkyl sulphoxides, etc.

The toothpaste formulations and the formulations to be chewed by the user will comprise the respective conventional base material and conventional adjuvant such as flavouring, sweetening and coloring agents, humectants, etc., as those mentioned above, and thickening and gelling agents such as thickening silica, natural or synthetic gums, e.g. tragacanth gum , guar gum, hydroxyethyl- and carboxymethyl cellulose, polyvinyl pyrrolidone, starch, etc.

The protein preparation according to the invention, in either liquid or solid form, should be used for purposes of prevention of periodontitis at least once, preferably twice a day. For purposes of treatment of periodontitis or other bacterial disorders the frequency of use can be increased to 3 to 4 times a day.

A protein mixture according to the present invention was prepared, called hereinafter FORMULA, comprising 75% of bovine serum albumin, 17% of lactoferrin, 5% of lysozyme from chicken egg and 3% of trypsin inhibitor from chicken egg, and was tested for antibacterial activity by placing both the FORMULA itself and individual proteins composing it in contact with two microorganisms chosen as representatives of the microbial flora that is commonly indicated as being responsible for the pathogenesis of periodontitis and of other tooth diseases. Antibacterial activity was also measured by using the free proteins in solution or bound to hydroxyapatite, a substance used as a model of the dental surface.

The protein FORMULA of above was also tested for anti-adhesive activity by measuring its ability to prevent the binding to hydroxyapatite, a substance used as a model of the dental surface, of two microorganisms chosen as representatives of the microbial flora commonly considered responsible for the pathogenesis of periodontitis and of other tooth diseases.

The following microorganisms, chosen as representatives of the microbial flora commonly considered responsible for the pathogenesis of periodontitis and of other tooth diseases, were used:

*Streptococcus mutans* ATCC 6715-13 grown in Todd Hewitt Broth (THB-BBL) at 37° C.

*Porphyromonas gingivalis* grown at 37 ° C. in brain-heart infusion broth (BHI-BBL) or other known culture media, with or without the addition of haemin (10 µg/ml) and vitamin K (1 µg/ml), using an anaerobe hood (FORMA-Scientific, Marietta, Ohio).

EXAMPLE 1

Antibacterial Activity

The antibacterial activity of the following protein preparations was assessed: lactoferrin, bovine serum albumin, salivary proteins, and the FORMULA of the present invention. The antibacterial activity of the above-mentioned protein preparations was assessed by using them in free form or adsorbed on hydroxyapatite. Efficiency was evaluated by microbial count in media suitable for the development of the test strains, with or without the addition of the described substances. The degree of antibacterial activity of the individual proteins, as well as of the formula itself, can vary according to the biochemical and culture conditions of the media in which testing occurs. Bacteriostatic activity can in fact be detected in culture media during microbial multiplication, whereas bactericidal activity can be already detected in the first hour of contact between bacteria and proteins in saline solution (PBS).

In a first test, $10^5$ cells/ml of *Streptococcus mutans* were added to the described culture medium, which contained respectively 1 mg/ml of lactoferrin (Lf) or 1 mg/ml of bovine serum albumin (BSA) or 1 mg/ml of salivary proteins (PS) or 6 mg/ml of the FORMULA according to the present invention, which contained 1 mg/ml of the respective transferrin.

After 6 hours of incubation under agitation at 37° C., the colony-forming units were counted (see Table 1a).

In a second test, $10^5$ cells/ml of *Streptococcus mutans* were added to the described culture medium, which contained respectively 1 mg/ml of lactoferrin (Lf) or 1 mg/ml of bovine serum albumin (BSA) or 1 mg/ml of salivary proteins (PS) or 6 mg/ml of the FORMULA according to the present invention, which contained 1 mg/ml of the respective transferrin. In this second experiment, the above-mentioned proteins had been kept in contact beforehand with 10 mg/ml of hydroxyapatite for 30 minutes at 37° C., in order to allow adsorption of the proteins on the hydroxyapatite.

After 6 hours of incubation under agitation at 37° C., the colony-forming units were counted (see Table 1a). The control, CTRL, consisted of the THB-BBL culture broth mentioned hereinabove, without protein additions.

In a third test, $10^5$ cells/ml of *Porphyromonas gingivalis* were added under anaerobic conditions to the described culture media, which contained respectively 1 mg/ml of lactoferrin (Lf) or 1 mg/ml of bovine serum albumin (BSA) or 1 mg/ml of salivary proteins (PS) or 6 mg/ml of the FORMULA according to the present invention, which contained 1 mg/ml as transferrin.

After 48 hours of incubation under anaerobic conditions at 37° C., the colony-forming units were counted (see Table 1b).

In a fourth test, $10^5$ cells/ml of *Porphyromonas gingivalis* were added under anaerobic conditions to the described culture media, which contained respectively 1 mg/ml of lactoferrin (Lf) or 1 mg/ml of bovine serum albumin (BSA)

or 1 mg/ml of salivary proteins (PS) or 6 mg/ml of the FORMULA according to the present invention, which contained 1 mg/ml as transferrin. In this fourth example, the above-mentioned proteins had been kept in contact beforehand with 10 mg/ml of hydroxyapatite for 30 minutes at 37° C., in order to allow adsorption of the proteins on the hydroxyapatite.

After 48 hours of incubation under anaerobic conditions at 37° C., the colony-forming units were counted (see Table 1b). The CTRL consisted of the BHI-BBL culture broth mentioned hereinabove.

TABLE 1a

Antibacterial activity after 6 hours of incubation at 37° C. under agitation. The inoculum consisted of 10 cells/ml of S. mutans.

|  | CTRL | Lf | BSA | PS | FORMULA |
|---|---|---|---|---|---|
| Free proteins Streptococcus mutans | $5 \times 10^8$ | $1 \times 10^6$ | $5 \times 10^8$ | $5 \times 10^6$ | $5 \times 10^4$ |
| Proteins adsorbed on hydroxyapatite | $5 \times 10^8$ | $5 \times 10^5$ | $5 \times 10^8$ | $2 \times 10^6$ | $2 \times 10^4$ |

TABLE 1b

Antibacterial activity after 48 hours of incubation at 37° C. under anaerobic conditions. The inoculum consisted of $10^5$ cells/ml of Porphyromonas gingivalis.

|  | CTRL | Lf | BSA | PS | FORMULA |
|---|---|---|---|---|---|
| Free proteins Porphyromonas gingivalis | $5 \times 10^5$ | $1 \times 10^5$ | $5 \times 10^5$ | $1 \times 10^4$ | $1 \times 10^4$ |
| Proteins adsorbed on hydroyapatite | $5 \times 10^5$ | $1 \times 10^5$ | $5 \times 10^5$ | $2 \times 10^4$ | $5 \times 10^3$ |

Naturally, the higher the antibacterial activity, the lower the number of microorganisms detected after incubation. The above-reported example clearly shows that the formula according to the present invention exhibits the maximum antibacterial activity both against Streptococcus mutans and against Porphyromonas gingivalis.

EXAMPLE 2

Anti-adhesive Activity

The anti-adhesive activity of the following proteins was assessed: lactoferrin, bovine serum albumin, salivary proteins, the FORMULA according to the present invention.

Columns with a diameter of 0.8 cm for low-pressure liquid chromatography, containing 1 g of hydroxyapatite in a phosphate buffer (PBS), were prepared.

After percolation of the protein solutions containing respectively 100 mg/10 ml of lactoferrin (Lf) or 100 mg/10 ml of bovine serum albumin (BSA) or 100 mg/10 ml of salivary proteins (PS) or 100 mg/10 ml of the FORMULA according to the present invention, the proteins that had not adhered were removed by washing with 100 ml of PBS. Appropriate dosages of the proteins in the eluate of the wash showed that 80% of the percolated proteins had remained adsorbed on the gram of hydroxyapatite contained in the chromatography column.

The chromatography columns were subsequently inoculated under aerobic or anaerobic conditions with a suspension containing $10^8$ cells of the strains of Streptococcus mutans or Porphyromonas gingivalis in a physiological solution. Washing with PBS (1000 ml) eluted the microorganisms that had not adhered to the hydroxyapatite.

A second wash with 100 ml of NaCl 1M allowed elution of the microorganisms adhered to the hydroxyapatite (Table 2). The controls in Table 2 consisted of the columns prepared as disclosed, i.e. of hydroxyapatite without addition of proteins.

TABLE 2

Anti-adhesive activity

|  | CTRL | Lf | BSA | PS | FORMULA |
|---|---|---|---|---|---|
| Streptococcus mutans |  |  |  |  |  |
| PBS wash | $7 \times 10^2$ | $9 \times 10^7$ | $9 \times 10^7$ | $5 \times 10^7$ | $1 \times 10^8$ |
| 1M NaCl wash | $9 \times 10^7$ | $1 \times 10^5$ | $6 \times 10^6$ | $4 \times 10^7$ | $1 \times 10^3$ |
| Porphyromonas gingivalis |  |  |  |  |  |
| PBS wash | $1 \times 10^2$ | $8 \times 10^7$ | $8 \times 10^7$ | $4 \times 10^7$ | $9 \times 10^7$ |
| 1M NaCl wash | $1 \times 10^8$ | $7 \times 10^6$ | $8 \times 10^6$ | $6 \times 10^7$ | $1 \times 10^4$ |

The higher the anti-adhesive ability of a substance, the lower the number of microorganisms eluted with 1M NaCl, since the microorganisms that had not adhered were washed away beforehand by PBS. The above example clearly shows that the formula according to the present invention exhibits the highest anti-adhesive ability both against Streptococcus mutans and against Porphyromonas gingivalis.

EXAMPLE 3

The antibacterial activity of various preparations according to the invention was evaluated with respect to individual components and to a control sample containing no protein compounds, tested according to the above-described experimental conditions (first and third tests of Example 1).

The proteins were added at the following concentrations: transferrin (TRF) 1 mg/ml; lysozyme (LYS) 0.3 mg/ml; protease inhibitors (INHIB) 0.20 mg/ml; albumin (ALB) 4.5 mg/ml. The control (CTRL) consisted of the culture broths used in said first and third tests of example 1, to which no protein was added.

| PROTEINS | S. mutans | P. gingivalis |
|---|---|---|
| CTRL | $5 \times 10^8$ | $5 \times 10^5$ |
| TRF | $1 \times 10^6$ | $1 \times 10^5$ |
| TRF + LYS | $1 \times 10^5$ | $5 \times 10^4$ |
| TRF + LYS + ALB | $1 \times 10^5$ | $5 \times 10^4$ |
| TRF + LYS + INHIB | $8 \times 10^4$ | $2 \times 10^4$ |
| TRF + LYS + ALB + INHIB | $5 \times 10^4$ | $1 \times 10^4$ |

The following examples show various ready-to-use forms of the preparations according to the invention.

EXAMPLE 4

Mouthwash

Composition per 100 ml
active ingredients:
Albumin, serum albumin from bovine serum, SIGMA A6793, 650 mg
Transferrin, ovotransferrin from chicken egg, SIGMA C1130, 200 mg Lysozyme, from chicken egg, SIGMA L2879, 100 mg
Trypsin inhibitor, from soy bean, SIGMA T9128, 50 mg
carriers, preservatives and flavouring agents:
Sodium chloride 1 g
Sodium bicarbonate 100 mg
Methyl-p-hydroxybenzoate 100 mg
Peppermint oil 50 mg
Purified water to 100 ml
use:
Two rinses a day, one in the morning, one in the evening.

EXAMPLE 5

Toothpaste
Composition per 100 g
active ingredients:
Albumin, serum albumin from bovine serum, SIGMA A6793, 1.5 g
Transferrin, lactoferrin from bovine milk, SIGMA L9507, 0.5 g
Lysozyme, from chicken egg, SIGMA L2879, 100 mg
Trypsin inhibitor, from chicken egg, SIGMA T9253, 50 mg
carriers, preservatives and flavouring agents:
Precipitated silica 15 g
Sodium benzoate 4 g
Sodium lauryl sulfate 2 g
Calcium phosphate 1.2 g
Sodium carrageenin 1.1 g
Titanium dioxide 1 g
Sodium mono-fluoro phosphate 0.3 g
Methyl-p-hydroxybenzoate 0.1 g
Peppermint oil 50 mg
Purified water to 100 g
use:
Use as a normal toothpaste twice a day, in the morning and evening.

EXAMPLE 6

Envelope Packs
Composition for 1 envelope
active ingredients:
Albumin, lactalbumin from bovine milk, SIGMA L5385, 150 mg
Transferrin, ovotransferrin from chicken egg, SIGMA C1130, 35 mg
Lysozyme, from chicken egg, SIGMA L2879, 10 mg
Trypsin inhibitor, from chicken egg, SIGMA T9253, 5 mg
carriers, preservatives and flavouring agents:
Sodium chloride 20 mg
Sodium bicarbonate 10 mg
Methyl-p-hydroxybenzoate 20 mg
Peppermint oil 5 mg
The ingredients are reduced to finely divided powder and thoroughly mixed on conventional grinding and mixing equipment.
use:
The content of an envelope is dissolved in 20 ml water for two rinse uses, one in the morning and one in the evening.

EXAMPLE 7

Chewing Gum
Composition of one piece of gum:
active ingredients:
Albumin, ovoalbumin from chicken egg, SIGMA A5253, 150 mg
Transferrin, serum transferrin from bovine serum, SIGMA T5761, 35 mg
Lysozyme, from chicken egg, SIGMA L2879, 10 mg
Trypsin inhibitor, from soy bean, SIGMA T9128, 5 mg
carriers, preservatives and flavouring agents:
Gum base (Paloya TX) 400 mg
Glucose 100 mg
Glycerol 10 mg
Sodium bicarbonate 10 mg
Methyl-p-hydroxybenzoate 20 mg
Peppermint oil 5 mg
use:
One piece of chewing gum after the main meals.

We claim:

1. Topical preparation for use in the prevention and therapy of diseases of the teeth and of the oral cavity caused by bacteria or adhesion of pathogenic species, characterized in that it comprises a mixture of proteins comprising at least one transferrin at a concentration of 5 to 95% by weight; at least one albumin at a concentration of 5 to 95% by weight; and at least one lysozyme at a concentration of 2 to 90% by weight.

2. Preparation according to claim 1, comprising a mixture of said at least one transferrin with at least one protease inhibitor and with at least one protein selected from lysozymes and albumins, wherein said inhibitor is present at a concentration of 1 to 20% by weight, said at least one transferrin and at least one lysozyme or at least one albumin being each present at a concentration of 5 to 94% by weight.

3. Preparation according to claim 1, wherein said protein mixture comprises 5 to 92% of said at least one transferrin, 5 to 92% of said at least one albumin, 2 to 80% of said at least one lysozyme, and 1 to 20% of said at least one protease inhibitor, said percentages being expressed by weight with respect to the weight of the protein mixture.

4. Preparation according to claim 3, wherein said protein mixture comprises 10 to 50% of said at least one transferrin, 40 to 84% of said at least one albumin, 5 to 30% of said at least one lysozyme and 1 to 10% of said at least one protease inhibitor.

5. Preparation according to claim 3, wherein said protein mixture comprises 15 to 25% of said at least one transferrin, 60 to 75% of said at least one albumin, 5 to 10% of said at least one lysozyme and 2 to 5% of said at least one protease inhibitor.

6. Preparation according to claim 1, wherein said proteins are selected from the group consisting of said proteins of natural origin, comprising proteins of human, animal and plant origin, proteins obtained by recombinant-DNA technology and chemically synthesized proteins.

7. Preparation according to claim 1, in a form selected from the group comprising a liquid preparation, a pasty preparation, a solid preparation and a preparation immobilized or adsorbed on an inert support.

8. Preparation according to claim 7 in the form of a mouthwash comprising from 0.1 to 10% w/v of said protein mixture in a solvent selected from water and ethanol-water mixtures.

9. Preparation according to claim 8 further comprising one or more adjuvants selected from humectants, sweeteners, flavouring agents, thickening agents, detergent builders, surfactants and antibacterial and antiplaque agents, acceptable for oral topical use.

10. Preparation according to claim 7 in a form selected from toothpaste and formulations to be chewed, comprising from 1 to 60% by weight of said protein mixture incorporated in a conventional base for a toothpaste or a formulation to be chewed.

11. Preparation according to claim 10 further comprising one or more adjuvants selected from thickening agents, humectants, sweeteners, flavoring agents, and antibacterial and antiplaque agents acceptable for oral topical use.

12. A method of using the preparation according to claim 1 for preventing and treating diseases of the teeth and of the oral cavity of a mammal caused by bacteria or adhesion of pathogenic species which comprises topically administering to said mammal an amount of the preparation according to claim 1 sufficient for preventing and treating diseases of the teeth and of the oral cavity caused by bacteria or adhesion of pathogenic species.

13. Preparation according to claim 1, further including at least one protease inhibitor.

* * * * *